United States Patent
Holzner et al.

(10) Patent No.: US 7,204,998 B2
(45) Date of Patent: Apr. 17, 2007

(54) PERFUMING OR FLAVORING MICROCAPSULES COMPRISING A FIREPROOFING AGENT

(75) Inventors: Günter Holzner, Grand-Lancy (CH); André Moser, Segny (FR)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 10/613,668

(22) Filed: Jul. 2, 2003

(65) Prior Publication Data

US 2004/0022821 A1 Feb. 5, 2004

Related U.S. Application Data

(63) Continuation of application No. PCT/IB02/04749, filed on Nov. 11, 2002.

(30) Foreign Application Priority Data

Nov. 22, 2001 (WO) .................. PCT/IB01/02210

(51) Int. Cl.
| | |
|---|---|
| A61K 8/18 | (2006.01) |
| A61K 8/19 | (2006.01) |
| A61K 9/00 | (2006.01) |
| A61K 8/02 | (2006.01) |
| A61K 9/16 | (2006.01) |
| A61K 9/50 | (2006.01) |
| A61L 11/00 | (2006.01) |

(52) U.S. Cl. .............. 424/490; 424/65; 424/70.1; 424/73; 424/76.7; 424/400; 424/401; 426/89; 510/119; 510/130; 510/276; 512/4

(58) Field of Classification Search ........... 424/400, 424/401, 490, 65, 70.1, 73, 76.7; 512/4; 510/119, 130, 276; 426/89
See application file for complete search history.

(56) References Cited

U.S. PATENT DOCUMENTS

| 3,445,563 | A |   | 5/1969  | Clegg ........................ 424/35 |
|---|---|---|---|---|
| 3,989,852 | A |   | 11/1976 | Palmer ...................... 426/289 |
| 4,597,959 | A | * | 7/1986  | Barr ......................... 424/401 |
| 4,812,445 | A | * | 3/1989  | Eden et al. .................. 514/60 |
| 4,908,233 | A | * | 3/1990  | Takizawa et al. ...... 427/213.35 |
| 5,098,725 | A | * | 3/1992  | Rotman et al. ............. 426/98 |
| 5,185,155 | A | * | 2/1993  | Behan et al. ............... 424/451 |
| 5,585,093 | A | * | 12/1996 | Murphy ..................... 424/65 |
| 5,614,179 | A | * | 3/1997  | Murphy et al. ............. 424/65 |
| 5,861,144 | A | * | 1/1999  | Peterson et al. ............ 424/65 |
| 6,056,949 | A |   | 5/2000  | Menzi et al. .............. 424/76.1 |
| 6,197,349 | B1| * | 3/2001  | Westesen et al. ........... 424/501 |
| 6,369,290 | B1| * | 4/2002  | Glaug et al. ............... 604/359 |
| 6,475,542 | B1| * | 11/2002 | Soeda et al. ................ 426/98 |
| 6,531,155 | B1| * | 3/2003  | Schade et al. .............. 424/489 |
| 6,555,098 | B1| * | 4/2003  | Murphy et al. ............. 424/65 |

FOREIGN PATENT DOCUMENTS

| EP | 0 070 719 B1 |   | 12/1985 |
|---|---|---|---|
| EP | 1 064 856 A2 | * | 1/2001 |
| WO | WO 9117821 A | * | 11/1991 |

\* cited by examiner

*Primary Examiner*—Sreeni Padmanabhan
*Assistant Examiner*—Marina Lamm
(74) *Attorney, Agent, or Firm*—Winston & Strawn LLP

(57) ABSTRACT

Perfuming or flavoring microcapsules that include a fireproofing agent in addition to a perfuming or flavoring ingredient and a carrier material, so that the microcapsules can reduce the occurrence or an explosion of reduced violence when suspended in hot air during their preparation. Also, methods of making these microcapsules and their use in perfumed, food, beverage or pharmaceutical products.

10 Claims, No Drawings

PERFUMING OR FLAVORING MICROCAPSULES COMPRISING A FIREPROOFING AGENT

CROSS-REFERENCE TO RELATED APPLICATIONS

This application is a continuation of International application PCT/IB02/04749 filed Nov. 11, 2002, the entire content of which is expressly incorporated herein by reference thereto.

TECHNICAL FIELD

The present invention relates to the field of perfumery and to the flavor industry. It concerns more particularly perfuming or flavoring microcapsules characterized by the fact that, when subjected to a sufficiently powerful ignition source, their rapid combustion reaction is weak or moderate. In fact, the microcapsules of the invention comprise an effective amount of a fireproofing agent susceptible of reducing the violence of their explosion, so as to classify these particles in a dust hazard class St-1.

BACKGROUND OF THE INVENTION

Microcapsules are employed to a large extent in the perfumery and flavoring industries. They constitute delivery systems for perfuming or flavoring ingredients and can be advantageously used in a very large number of applications. The encapsulation of active substances such as perfuming or flavoring ingredients provides at the same time a protection of the ingredients there-encapsulated against "aggressions" such as oxidation or moisture and allows, on the other hand, a certain control of the kinetics of flavor or fragrance release to induce sensory effects through sequential release.

Now, the numerous advantageous properties of microcapsules in these fields are opposed to other properties that must be taken into account during their preparation, transportation, storage and handling. In fact, such delivery systems, due to their nature, and in particular to the fact that they encapsulate volatile and flammable substances, constitute combustible dusts which can, when dispersed in air or another oxygen-containing gas, form readily ignitable mixtures. When ignited by a sufficient powerful ignition source, the result is a rapid combustion reaction with advancing pressure and flame front.

This issue becomes important during the preparation of microcapsules. In particular, spray-drying and fluidized-bed encapsulation processes are highly concerned by this issue, as they are both based on the use of an equipment wherein particles are suspended in hot air as fine particles and can therefore undergo explosion during their preparation.

Spray-drying is the most common encapsulation technique used to stabilize volatile substances such as flavors or fragrances, by encapsulating them in a solid form that is suited to many applications. Spray-dried powders are commonly made in the usual spray-drying equipment. Spray-drying is usually effected by means of a rotating disc or of multi-component nozzles. Detailed techniques are described for instance in K. Masters, Spray-drying Handbook, Longman Scientific and Technical, 1991.

Fluidized beds are used for spraying a coating on a core material fluidized in a bed. This encapsulation technique is also well known and is described for instance in EP 70719 or in U.S. Pat. No. 6,056,949, the contents of the latter of which is hereby expressly included herein by reference to the extent necessary to understand this technique.

Both above-described encapsulation equipments are susceptible to explosions of particles suspended in the air, so that they thus have to be adapted as a function of the technical safety parameters characterizing the particles there-treated. In particular, they have to be dimensioned as a function of the violence of explosions that can occur during the preparation of microcapsules. Therefore, the problem of reducing the violence of possible explosions of powder products resulting from such encapsulation processes is of paramount importance for the industry.

For the safe handling of combustible substances, it is imperative to know the dangerous properties of a product. One reliable way to characterize the combustible and explosive properties of a product is to subject a sample of the product to various tests and classify the results in accordance with the technical safety characteristics. The international standards (VDI Guideline 2263 part 1: Dust Fires and Dust Explosions, Hazard Assessment—Protective Measures, Test Methods for the Determination of Safety Characteristics of Dusts, Beuth, Berlin, May 1990) describe the test equipments (Modified Hartmann apparatus and Close apparatus) and methods. These methods allow to determine physical constants such as the maximum explosion behavior of a combustible dust in a closed system. A pyrotechnic igniter with a total energy of 10 kJ is used as ignition source. From test methods described in the mentioned guidelines, a characteristic constant, $K_{St}$, which is dust specific, is determined. As there are so many such dusts produced and processed in industrial practice, for example for pharmaceutical and cereal or flour products, it is appropriate to assign this maximum explosion constant to one of the several dust explosion classes and to use these as a basis for the dimensioning of constructional protective measures. The correspondence between these classes hereafter referred as dust hazard classes, and the constant $K_{St}$ is the following:

| Dust Hazard Class | Product Specific Constant $K_{St}$ [bar.m.s$^{-1}$] |
| --- | --- |
| St-1 | >0 to 200 |
| St-2 | <200 to 300 |
| St-3 | <300 |

Now, despite that some perfuming and flavoring ingredients are classified in a dust hazard class St-1, a large number of these ingredients and thus the microcapsules encapsulating them, and depending on the volatility of the perfuming or flavoring ingredients, are still classified under an St-2 dust hazard class and thus require production equipment specifically adapted to contain or withstand the violence of possible explosions, which of course can be very costly.

While solutions have been proposed for solving similar problems in other technical fields, such as for instance for polymeric organic compositions which demonstrate a tendency to degrade, the perfuming and flavoring industry was never provided with an efficient solution, adapted to these products and which would solve the economic problem related to the costly equipment required to prepare St-2 classified microcapsules. The present invention now provides a solution to this problem.

SUMMARY OF THE INVENTION

The inventors have established that fireproofing agents could be added directly to perfuming and flavoring microcapsules in an amount effective to reduce the violence of possible explosions during their preparation, in particular when suspended in hot air. Thus, the invention relates to perfuming or flavoring microcapsules comprising at least one perfuming or flavoring ingredient dispersed in or adsorbed within a polymeric carrier material, with the microcapsules comprising an effective amount of a fireproofing agent susceptible of reducing the dust hazard explosive class of the microcapsules to St-1. The invention also relates to methods of making and using such microcapsules.

DETAILED DESCRIPTION OF THE PREFERRED EMBODIMENTS

As mentioned above, the St-class of a microcapsule is deduced from the value of its product specific constant $K_{-St}$ (see correspondence Table above). The $K_{-St}$ parameter is measured by means of a Modified Hartmann apparatus and Close apparatus. This equipment and the methods of measurement of $K_{-St}$ are described in International standards that are well known to the skilled artisan and are identified as (VDI Guideline 2263 part 1: Dust Fires and Dust Explosions, Hazard Assessment—Protective Measures, Test Methods for the Determination of Safety Characteristics of Dusts, Beuth, Berlin, May 1990).

The perfuming or flavoring microcapsules of the invention comprise an effective amount of a fireproofing agent which is capable of reducing the violence of the explosion of the microcapsules possibly induced by their suspension in the air during their preparation. This is very advantageous considering that such delivery systems are mainly composed of highly volatile ingredients which constitute therefore combustible dust. Such volatile ingredients had to be used in the past in limited proportions in compositions subjected to processes involving the suspension of particles in hot air. Now, the solution provided by the present invention allows to use higher quantities of these ingredients, and therefore provides an advantageous alternative to the prior use of precursors of certain particularly volatile ingredients.

The invention therefore provides an advantageous solution as regards the problem of the preparation of perfuming and flavoring microcapsules and powder products, in particular for preparations via processes involving a spray-drier or a fluidized bed, wherein fine particles are suspended in the air and are therefore more susceptible of exploding. Under an St-1 class, the violence of the explosion will be a weak or at least moderate reaction, whereas it would be a strong reaction for a dust hazard class St-2, and a very strong reaction for a dust hazard class St-3. As a consequence, the equipment used for the preparation of microcapsules according to the present invention can be dimensioned accordingly i.e. as St-1 and thus become less costly, whilst guaranteeing the same or better manufacture safety conditions.

Furthermore, the microcapsules and powder products of the invention not only present an advantage as regards the violence of any possible such reaction induced during their preparation, but also have proved to be less sensitive to ignition, i.e. to present a reduced tendency to explode. This characteristic may be measured and is expressed through the minimum ignition energy or MIE parameter. The MIE of a dust is defined as the lowest quantity of electrical energy stored in a capacitor which, when discharged over a spark gap, is just not sufficient to ignite the most readily ignitable dust or air mixture in a series of twenty consecutive tests, at atmospheric pressure, ambient temperature and lowest turbulence possible. The international standards (VDI Progress Report 134) state that dusts with a minimum ignition energy between 10 and 100 mJ are generally regarded as having normal ignitibility, whereas, in the case of dusts with a minimum ignition energy below 10 mJ, particular attention must be paid to eliminate all sources of ignition, even weak ignition sources such as mechanical sparks or discharges of static electricity.

The method for measuring a MIE parameter is described in International standards, hereby included by reference, namely VDI Guidelines 2263, part 1: Dust Fires and Dust Explosions, Hazard Assessment—Protective Measures, Test Methods for the Determination of Safety Characteristics of Dusts, Beuth, Berlin, May 1990.

As regards the industry here-concerned, it turns out that some perfuming and flavoring powders possess, due to the nature of perfuming and flavoring ingredients, MIE values in the range of 1 to 10 ml. Now, it turned out that, in a totally unexpected manner and as shown in the example below, the presence of a fireproofing agent in the composition of the microcapsules of the invention resulted in an increase in the MIE characterizing values of these products, which thus reached a value above 10 mJ. This is an unexpected advantage of the invention which is moreover of paramount importance, as the microcapsules of the invention, besides their facilitated process of preparation, now present also numerous advantages as regards the requirements for their storage or even their transport, and further handling.

The fireproofing agent of the invention is preferably selected from the group consisting of sodium silicate, potassium silicate, sodium carbonate, sodium hydrogen carbonate, monoammonium phosphate or carbonate, diammonium phosphate, mono-, di- or trisodium phosphate, sodium hypophosphite, melamine cyanurate, chlorinated hydrocarbons and mixtures thereof. Examples of commercial products of this kind include Monnex® (origin: SICLI Matériel Incendie SA, Geneva, Switzerland), Bi-Ex® (origin: SICLI Matériel Incendie SA, Geneva, Switzerland), ABC-E® (origin: SICLI Matériel Incendie SA, Geneva, Switzerland), Tropolar® (origin: SICLI Matériel Incendie SA, Geneva, Switzerland) and ATO-33® (origin: SICLI Matériel Incendie SA, Geneva, Switzerland).

The fireproofing agent is usually present in a proportion representing from 5 to 90% by weight of the total dry weight of the microcapsule. Preferably, it will represent from 5 to 15% by weight relative to the total dry weight of the microcapsule.

The microcapsule of the invention is based on the presence of at least one perfuming or flavoring material and a polymeric carrier material.

The perfuming or flavoring ingredient, in the form of one sole ingredient or in the form of a composition, either in isolation or, optionally, in a solution or suspension in solvents and adjuvants of current use, represents from 1 to 80%, and preferably from 1 to 50% by weight relative to the total weight of the microcapsule. The terms perfume or flavor ingredient or composition as used herein are deemed to define a variety of fragrance and flavor materials of both natural and synthetic origins. They include single compounds and mixtures. Specific examples of such components may be found in the current literature, e.g. in Perfume and Flavor Chemicals by S. Arctander, Montclair, N.J. (USA); Fenaroli's Handbook of Flavor Ingredients, CRC Press or Synthetic Food Adjuncts by M. B. Jacobs, van Nostrand Co.

Inc., and other similar text books; and are well-known to the person skilled in the art of perfuming, flavoring and/or aromatizing consumer products, i.e., of imparting an odor or a taste to a consumer product.

In one embodiment of the invention, the >perfume or flavor ingredient or composition is dispersed in a polymeric carrier material. Non limiting examples of the latter include polyvinyl acetate, polyvinyl alcohol, dextrins, natural or modified starch, vegetable gums, pectins, xanthanes, alginates, carragenans or yet cellulose derivatives such as for example carboxymethyl cellulose, methylcellulose or hydroxyethylcellulose, and generally all materials currently used for encapsulation of volatile substances.

In another embodiment, the perfume or flavor ingredient or composition is adsorbed within a polymeric carrier material. As non-limiting examples of the latter, one can cite amorphous silica, precipitated silica, fumed silica and aluminosilicates such as zeolite and alumina.

The method for preparing these of perfuming and flavoring microcapsules include several alternatives. In a first embodiment, the fireproofing agent is added to an aqueous emulsion consisting of the perfuming or flavoring ingredient or composition dispersed in the polymeric carrier material. The obtained emulsion is then spray-dried in order to form a powder. Optionally, an emulsifier may be added to the initial emulsion. This encapsulation technique does not require a more detailed description herein, as it relies on conventional spray-drying techniques, which are perfectly well documented in the prior art, such as is described, e.g., in the Spray-Drying Handbook, 3rd ed., K. Masters; John Wiley (1979), and as is currently applied in the food industry or in the flavor and perfume industries.

In another embodiment, the fireproofing agent, in the form of a solid powder, is simply blended with a spray-dried powder formed from the aqueous emulsion of perfuming or flavoring ingredient or composition in the polymeric carrier material and the emulsifier.

A third alternative for the preparation of the microcapsules of the invention to obtain an explosion reaction of reduced violence, is to firstly adsorb the perfuming or flavoring ingredient or composition within a porous polymeric carrier material as described above and to further coat the resulting system with a fireproofing agent. This method of preparation can be carried out in a fluidized bed apparatus, according to conventional techniques such as those described for instance in EP 70719 or in U.S. Pat. No. 6,056,949. The particles formed by adsorption of a fragrance or flavor ingredient or composition within the carrier can thus be coated after granulation, e.g., by spraying a solution, emulsion or melt of the fireproofing agent, which forms a protective film around the core.

During the granulation process, there can also be used usual additives such as artificial sweeteners, food dyes, vitamins, antioxidants, anti-foam agents, carbonic acid generators, or additional flavorants etc. which can be added to the core material or to the spray emulsion.

The microcapsules of the invention have an average diameter varying from usually 5 to 500 μm.

The microcapsules of the invention can advantageously be used to impart, improve, enhance or modify the organoleptic properties of a great variety of edible or perfumed end products. In the field of perfumery, the perfuming microcapsules resulting from any embodiment of the process according to the invention can be incorporated in a perfuming composition such as a perfume, a Cologne or an after-shave lotion, or yet they can be added to functional products such as detergents or fabric softeners, soaps, bath or shower gels, deodorants, body lotions, shampoos and other hair-care products, household cleansers, cleaning and deodorizing blocks for toilet tanks. On the other hand, in the case of flavors encapsulated, the consumer products susceptible of being flavored by the microcapsules of the invention may include foods, beverages, pharmaceuticals and the like.

The concentrations in which the microcapsules of the invention can be incorporated in such consumer products vary in a wide range of values, which are dependent on the nature of the product to be perfumed or flavored. Typical concentrations, to be taken strictly by way of example, are comprised in a range of values as wide as from a few ppm up to 5 or 10% of the weight of the flavoring or perfuming composition or finished consumer product into which they are included.

EXAMPLES

The invention will be now illustrated but not limited by way of the following examples wherein temperatures are given in degrees centigrade and abbreviations have the meaning common in the art.

Example 1

Dry Blending of a Spray-dried Perfuming Powder and a Powdered Fireproofing Agent An emulsion of the following composition was spray-dried in a spray-drier Büichi (origin: Switzerland):

| Ingredients | grams |
| --- | --- |
| Water | 150.0 |
| Capsul ®[1] | 67.0 |
| Perfume concentrate[2] | 33.0 |
| Total | 250.0 |

[1] dextrin dioctenylsuccinate; origin: National Starch, USA
[2] origin: Firmenich SA, Geneva, Switzerland The theoretical yield after evaporation of water was of 100 g of powder containing 33% of perfume.

The explosive character of the powder was measured with a Hartmann apparatus (see VDI Guideline 2263 part 1: Dust Fires and Dust Explosions, Hazard Assessment—Protective Measures, Test Methods for the Determination of Safety Characteristics of Dusts, Beuth, Berlin, May 1990), and the powder was attributed a dust hazard class St-2. The same powder was then mixed with diammonium phosphate in a powder form, in a ratio of 80:20.

The analysis of the explosive character of the homogeneous mixture, made under the same condition demonstrated that the mixture could be classified as St-1.

Example 2

Coating of Combustive Perfuming Microcapsules with Sodium Silicate

Silica dioxide spheres (Tixosil 68; origin: Rhodia, France) were filled with the perfuming ingredient described in Example 1 and further coated with sodium silicate as follows:

Adsorption of Perfume in Silica Dioxide

Thanks to its porous character, the silica dioxide adsorbed 60% of perfume and still stayed as a free-flowing granule without external liquid.

The explosive analysis measured as explained in Example 1 classified the mixture as St-2. The latter was then coated into a Kugelcoater (origin: Hüittlin, Germany) with sodium silicate, according to the following formula:

| Ingredients | grams |
|---|---|
| Tioxil 68 and perfume | 900 |
| Aqueous sodium silicate solution 35% | 300 |
| Total | 1200 |

After evaporation of water during the coating in the Kugelcoater, there were obtained about 1000 g of coated spheres coated with a sodium silicate layer.

The explosive analysis in a Hartmann apparatus classified the product as St-1. This result is a clear demonstration of the action of the sodium silicate protective layer.

Example 3

Spray-drying of a Perfuming Emulsion Comprising a Fire-proofing Agent

Two perfuming emulsions were prepared from the following formulas (parts by weight):

| Ingredients | Formula A (parts by weight) | Formula B (parts by weight) |
|---|---|---|
| Lavender perfume[1] | 13.20 | 13.20 |
| Tween ® 20[2] | 0.12 | 0.12 |
| Water | 60.00 | 60.00 |
| Citric acid | 0.12 | 0.12 |
| Capsul ®[3] | 20.56 | 26.56 |
| Budit ® 315[4] | 2.00 | — |
| Monoammonium phosphate | 4.00 | — |
| Total | 100.00 | 100.00 |

[1]origin: Firmenich SA, Geneva, Switzerland
[2]polyoxyethylene monolaurate; origin: ICI Chemicals, Great Britain
[3]dextrin dioctenylsuccinate; origin: National Starch, USA
[4]melamine cyanurate; origin: Budenheim, Germany The ingredients above-cited were homogenized by means of a Silverson type fast stirrer. The mixtures were then spray-dried in a Sodeva apparatus with an emulsion output of 2 kg/h, drying air: 320 m$^3$/h at 350° C. and 0.45×10$^5$ Pa.

There were thus obtained fine powders, the diameter of the particles being comprised between 10 and 300 μm and the content of liquid perfume being 13.2% by weight. After measuring the dust hazard class, as explained in Example 1, of the 2 kinds of powders, Formula A was classified as St-1, while Formula B was classified as St-2. Furthermore, the minimal ignition energy (MIE) was measured for both powders (for method used, see VDI Guideline 2263 part 1: Dust Fires and Dust Explosions, Hazard Assessment—Protective Measures, Test Methods for the Determination of Safety Characteristics of Dusts, Beuth, Berlin, May 1990). Formula A had a MIE comprised between 10 and 25 mJ, while Formula B had an MIE comprised between 5 and 10 mJ.

The latter was thus classified as very reactive (very low values for its MIE) and thus should be treated as a flammable gas (such as propane or butane). On the other hand, Formula A which possessed higher values for its MIE, would thus not be ignited by electric discharges.

Example 4

Spray-drying of a Flavoring Emulsion Comprising a Fire-proofing Agent

Two flavoring emulsions were prepared form the following formulas (parts by weight):

| Ingredients | Formula A (parts by weight) | Formula B (parts by weight) |
|---|---|---|
| Basilic flavor[1] | 16.33 | 16.33 |
| Acetaldehyde | 1.81 | 1.81 |
| Water | 45.02 | 45.02 |
| Capsul ®[2] | 28.59 | 36.84 |
| Disodium phosphate | 8.25 | — |
| Total | 100.00 | 100.00 |

[1]origin: Firmenich SA, Geneva, Switzerland
[2]dextrin dioctenylsuccinate; origin: National Starch, USA The ingredients above cited were homogenized by means of a fast stirrer.

The mixtures were then spray-dried in an APV PSD 52 apparatus with an emulsion output of 1 kg/h; inlet temperature of 180°; outlet temperature of 80°; evaporation capacity of 20 kg/h at 300°.

There were thus obtained fine powders, the mean particle sizes being respectively 45 μm (Formula A) and 37 μm (Formula B), and the flavor content of the spray-dried powders being identical to that of the starting emulsions.

After measuring the respective dust hazard classes of the obtained powders, as explained in Example 1, Formula A was classified as St-1, while Formula B was classified as St-3. Therefore the presence of an effective amount of disodium phosphate in Formula A advantageously reduced the dust hazard explosive class of the powder.

Furthermore, the evaluation of the two powders by an expert flavorist revealed that the flavor of the powder of formula A was not altered by the presence of disodium phosphate.

What is claimed is:

1. A spray-dried perfuming or flavoring microcapsule comprising at least one perfuming or flavoring ingredient dispersed in or adsorbed within a polymeric carrier material, wherein the microcapsule further comprises an effective amount of a fireproofing agent susceptible of reducing the dust hazard explosive class of the microcapsule to an St-1 classification, wherein said fireproofing agent is selected from the group consisting of sodium silicate, potassium silicate, monoammonium phosphate or carbonate, diammonium phosphate, mono-, di- or trisodium phosphate, sodium hypophosphite, melamine cyanurate, and mixtures thereof.

2. The perfuming or flavoring microcapsule according to claim 1, which comprises from 5 to 90% by weight of fireproofing agent relative to the dry weight of the microcapsule.

3. The perfuming or flavoring microcapsule according to claim 1, which comprises from 5 to 15% by weight of fireproofing agent relative to the dry weight of the microcapsule.

4. The perfuming or flavoring microcapsule according to claim 1, which comprises from 1 to 80% by weight of perfume or flavor relative to the total weight of the microcapsule.

5. The perfuming or flavoring microcapsule according to claim 1, which comprises from 1 to 50% by weight of perfume or flavor relative to the total weight of the microcapsule.

6. A method for the preparation of perfuming or flavoring microcapsules as defined in claim 1, which comprises adding a fireproofing agent to an aqueous emulsion of the perfuming or flavoring ingredient in the carrier polymeric material, and spray-drying the obtained emulsion to form a powder.

7. A perfumed product selected from the group consisting of a perfume, a Cologne, an after-shave lotion, a soap, a bath or shower gel, a deodorant, a body lotion, a shampoo or another hair-care product, a detergent, a fabric softener, a household cleaner and a cleaning and deodorizing block for toilet tanks, which further comprises perfuming microcapsules according to claim 1.

8. A perfumed product selected from the group consisting of a perfume, a Cologne, an after-shave lotion, a soap, a bath or shower gel, a deodorant, a body lotion, a shampoo or another hair-care product, a detergent, a fabric softener, a household cleaner and a cleaning and deodorizing block for toilet tanks, which includes perfuming microcapsules made according to the method of claim 6.

9. A food, beverage or pharmaceutical product, which includes flavoring microcapsules according to claim 1.

10. A food, beverage or pharmaceutical product, which includes flavoring microcapsules made according to the method of claim 6.

* * * * *

UNITED STATES PATENT AND TRADEMARK OFFICE
CERTIFICATE OF CORRECTION

PATENT NO. : 7,204,998 B2 Page 1 of 1
APPLICATION NO. : 10/613668
DATED : April 17, 2007
INVENTOR(S) : Holzner et al.

It is certified that error appears in the above-identified patent and that said Letters Patent is hereby corrected as shown below:

Column 8:
Line 54 (claim 1, line 11), after "hypophosphite," delete "melaminc" and insert -- melamine --.

Column 9:
Line 7 (claim 6, line 3), before "fireproofing agent", delete "a" and insert -- the --.

Signed and Sealed this

Nineteenth Day of June, 2007

JON W. DUDAS
*Director of the United States Patent and Trademark Office*